United States Patent [19]

Anderer et al.

[11] Patent Number: 5,892,458
[45] Date of Patent: Apr. 6, 1999

[54] APPARATUS FOR RECOGNITION OF EXCHANGEABLE PARTS IN ANALYTICAL MEASURING INSTRUMENTS

[75] Inventors: Herbert Anderer; Christian Buettner, both of Waldbronn; Bernd Walter Hoffmann; Claus Lueth, both of Karlsruhe, all of Germany

[73] Assignee: Hewlett-Packard Company, Palo Altro, Calif.

[21] Appl. No.: 724,882

[22] Filed: Oct. 3, 1996

[30] Foreign Application Priority Data

Oct. 31, 1995 [DE] Germany ............ 195 40 527.7

[51] Int. Cl.[6] ................ G01R 1/00; H04B 7/00
[52] U.S. Cl. ................ 340/825.54; 340/825.49; 210/600; 210/656; 210/659; 73/23.2; 73/23.35; 95/82; 95/83; 95/85; 96/106
[58] Field of Search ............... 340/825.54, 825.49, 340/505, 572, 573; 342/44, 52, 51; 210/600, 656, 659; 73/23.2, 23.35; 95/82, 83, 85; 96/105

[56] References Cited

U.S. PATENT DOCUMENTS

| 4,454,582 | 6/1984 | Clearly et al. | 364/427 |
|---|---|---|---|
| 4,935,875 | 6/1990 | Shah et al. | 364/497 |
| 4,975,647 | 12/1990 | Downer et al. | 324/425 |
| 5,191,610 | 3/1993 | Hill et al. | 380/21 |
| 5,420,592 | 5/1995 | Johnson | 342/357 |
| 5,420,794 | 5/1995 | James | 364/436 |
| 5,691,635 | 11/1997 | Pot et al. | 324/115 |

FOREIGN PATENT DOCUMENTS

| 0395188A1 | 4/1990 | European Pat. Off. . |
|---|---|---|
| 0672906A1 | 3/1995 | European Pat. Off. . |
| 4312093A1 | 4/1992 | Germany . |
| 4337515A1 | 11/1993 | Germany . |
| 4406256A1 | 2/1994 | Germany . |
| 4410781A1 | 3/1994 | Germany . |
| 4301401A1 | 7/1994 | Germany . |
| 9416270 | 1/1995 | Germany . |
| 19521044A1 | 6/1995 | Germany . |

*Primary Examiner*—Michael Horabik
*Assistant Examiner*—Yonel Beaulieu

[57] ABSTRACT

An apparatus for the recognition of exchangeable parts in an analytical measuring instrument or in an analytical measurement system with several analytical devices, which contain exchangeable parts has identification modules each attached to an exchangeable part, and transmit-receive devices which can receive information signals from an identification module and send information signals to an identification module, and a control device which evaluates the information from an identification module. The control device can cause a message to be displayed on a display device, if the information read out from an identification module does not fulfill certain conditions, for example with regard to the quality of the corresponding part.

8 Claims, 4 Drawing Sheets

APPARATUS FOR RECOGNITION OF EXCHANGEABLE PARTS IN ANALYTICAL MEASURING INSTRUMENTS

The invention relates to an apparatus for the recognition of exchangeable parts in analytical measuring instruments. Exchangeable parts of this kind include for example separation columns in liquid chromatography or in capillary electrophoresis, sample vessels, sample trays, pump heads of a fluid chromatograph, sample injection capillaries, detector cells or lamps in a spectrometer.

Analytical measurement technology comprises among other things a series of separation methods such as gas chromatography, liquid chromatography, supercritical liquid chromatography, capillary electrophoresis, capillary electrochromatography and sample identification methods such as spectrophotometry, fluorescence spectrometry, electrochemical methods. The measuring instruments used by these separation techniques and detection methods for detecting sample substances largely function automatically. These measuring instruments generally contain parts which after a certain period of use have to be replaced. For example, the separation column in a fluid chromatograph and lamps in spectrometers are spent after being used for a certain length of time and must be replaced by new parts. Other parts in analytical measuring instruments, such as detector cells, are exchangeable in order to be able to adapt equipment to special applications, for example to increase measurement sensitivity.

Although the condition of such exchangeable parts may considerably influence the measurement and the quality of the results, information about their condition is generally not taken into account in the measurement. Today, this is of particular interest in the context of the certification of laboratory methods. A weak point in certification is the fact that there is no recognition of, nor feedback about, passive exchangeable parts which typically possess no further means of electronic data exchange (for instance, mechanical parts).

DE-A-4301401 makes known an apparatus for the electronic and contact-free identification of chromatographic separation columns, with an electronic component which is connected to the separation column and with a read-write device which can read out and further process the information on the electronic component by electromagnetic means. Another column identification apparatus is known from U.S. Pat. No. 4,975,647.

In view of the state of the art the object of the invention is to create an apparatus according to the preamble of claim 1 which guarantees increased reliability and operational safety in conducting analytical measurements.

According to the invention this object is achieved for an apparatus according to the preamble by the characterizing features of claim 1.

According to claim 4 an exchangeable part of an analytical instrument can be exchanged automatically if it no longer meets certain conditions, for example if it no longer functions satisfactorily, or if the configuration of the analysis system has to be changed.

According to claim 7 an analytical measurement system with several analytical instruments is also created by means of the invention, in which the analytical instruments have exchangeable parts with corresponding identification modules, and in which there is a control device which evaluates the information read out from the identification modules using transmit-receive devices and is used for controlling the measurement system. The information stored on the identification modules is updated or added to when necessary. Among other things, a measurement system of this kind is characterized in that it enables reliable automatic processing of complex analysis sequences with a large number of samples and with different separation methods.

In the following, embodiment examples of the invention will be described in more detail with reference to the drawings.

Figure 1:
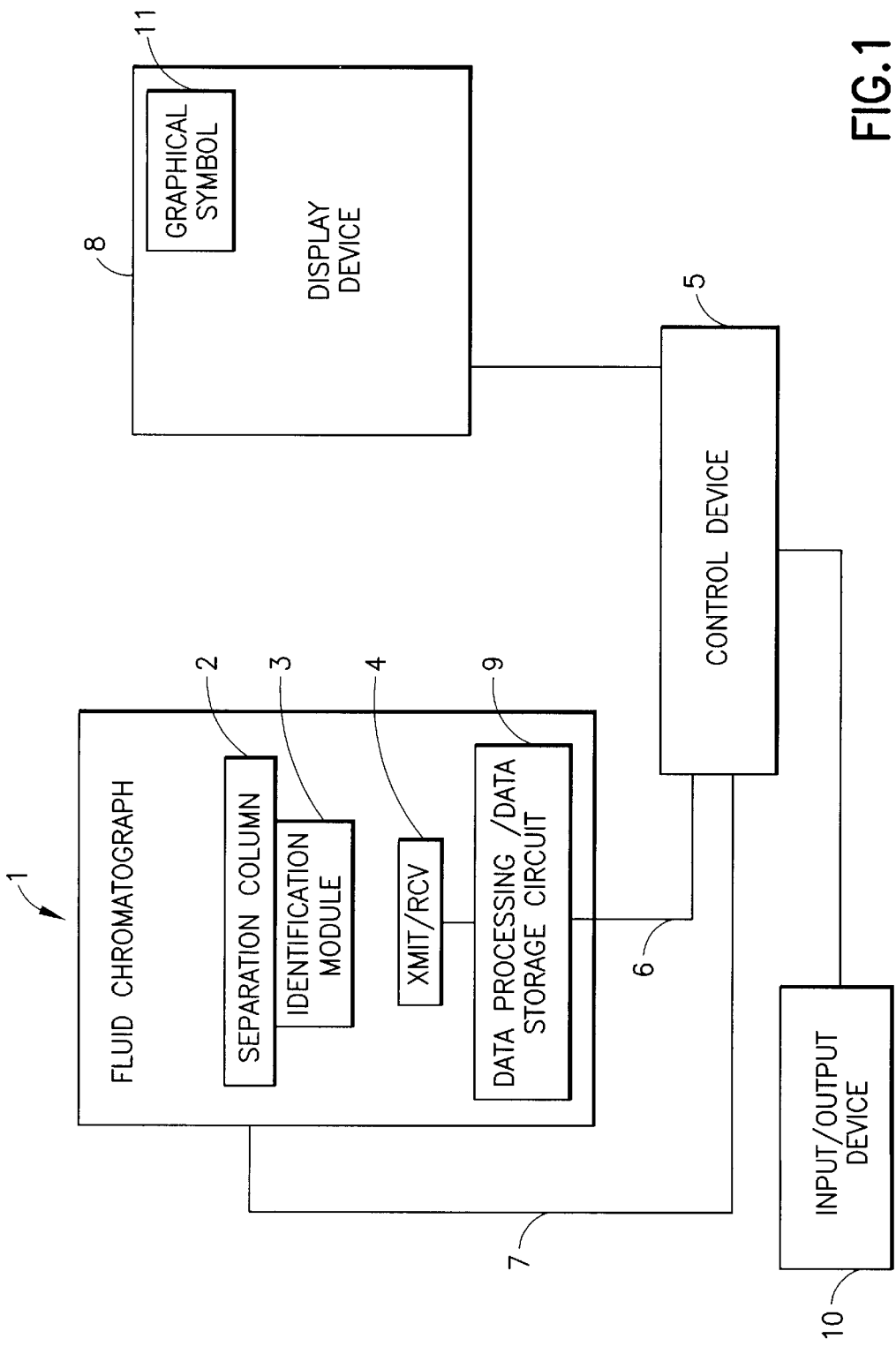
FIG. 1 is a schematic depiction of a first embodiment example of the present invention in conjunction with a chromatographic column.

FIG. 1 is a schematic depiction of a fluid chromatograph 1. An essential component of the fluid chromatograph is the separation column 2, from which different sample substances emerge in a certain time sequence. Further components of a fluid chromatograph 1, which for reasons of clarity are not shown, are a sample injection device and a high-pressure pump, which bring the sample and a solvent up to a high pressure before they enter the column 2. The substances emerging from the separation column 2 in a certain time sequence are then detected in a detector (not shown).

Separation column 2 is normally arranged in the chromatograph so that it is easily accessible from outside by the user, in order to enable it to be exchanged easily. An exchange is required for example if the column is spent. In addition, for a specific separation problem, separation of the sample substances may be improved by replacing a column of a certain column type with one of a different type; in this case exchanging the column is also necessary. Column 2 can be arranged in a thermostat-controlled chamber (column oven), in which different temperatures can be set in order to optimize the separation process.

As shown schematically in FIG. 1, a column identification module 3 is attached to column 2. The identification module 3 can for example be molded in a plastic clamp device which is clamped to column 2. Preferably, the identification module 3 contains a chip (e.g. EEPROM) which allows information to be read out, to be read in and to be deleted.

Opposite the identification module 3 a transmit-receive device 4 is arranged which can receive information from the identification module 3 and send information to it. Preferably, transmission of information takes place without any cable. The transmit-receive device 4 is connected to the device electronics belonging to the chromatograph. By means of the device electronics 9 and a control cable 6 the transmit-receive device 4 is connected to a control device 5, which in a preferable embodiment example is also employed to control the other functions of the chromatograph via a control cable 7. These functions include for example injection of the samples and the collection of the chromatographic measurements as well as possibly the analysis and further processing of the measurements.

The chromatographic measurements can be displayed on a display device 8 which is connected to the control device 5. As a display device, for example, the screen of a computer, of which the control device 5 also forms a part, can be used. As well as for displaying chromatographic measurements the display device 8 can also be used for representing operational conditions of the different components of the chromatograph. Finally, it is also possible for the user to trigger certain functions of the chromatograph via the screen 8, for instance by selecting a certain icon on the screen with the aid of a computer mouse, whereby a corresponding control instruction is sent from the control device to the chromatograph.

The column identification module 3 contains a large amount of information about the column 2, for example: stationary phase, particle size, column geometry, column dead volume, product number, serial number, maximum pressure, maximum temperature, maximum pH value, number of injections conducted each time, comments of the user. Information which changes, such as the number of injections, is automatically updated, whereby the control device 5 sends the appropriate signals to the transmit-receive device 4, which in turn enters them on the identification module 3.

According to one embodiment example of the invention, transmission of information between the transmit-receive device 4 and the identification module 3 is conducted by means of high-frequency signals. The identification module 3 comprises a receive circuit for receiving signals from the transmit-receive device 4, a transmit circuit for sending information to the transmit-receive device 4 and a data processing and data storage circuit 9, which typically comprises an EEPROM. The electrical energy required for running the identification module 3 is supplied by the high-frequency signals transmitted by the transmit-receive device 4. According to a practical example of the invention a commercially available "programmable identification transponder" can be used for the identification module.

According to one characteristic of the present invention, at regular intervals the transmit-receive device 4 sends a query signal to the column identification module 3, which then sends back a reply signal to the transmit-receive device 4. The reply signal sent by the identification module may for example correspond to the characteristic serial number for the column concerned. If no reply signal is received by the transmit-receive device 4, this means that the column along with the identification module 3 has been removed. If the reply signal is received, but does not match the serial number, this means that the column used so far has been exchanged for a different column. If the control device 5 detects one of these two conditions, it causes an appropriate message to be issued for the user on the display device 8. For example, an appropriate text or a graphical symbol or a combination of the two can be shown on the screen.

If with the aid of the control device 5 it has been determined that the column has been exchanged, this is shown for one thing on the screen 8 in a form visible to the user, and the data stored on the identification module of the new column also continues to be displayed on the screen. Thus, the user is informed, for example, about the type of column and its history, for instance the number of injections. In addition, it is important for the user to know that there is actually a column in place, because otherwise no separation can take place. An altogether safe method of operation is achieved.

According to a further characteristic of the invention the data stored on the identification module 3 is continually updated according to the operational conditions to which the column is exposed. Thus, the "curriculum vitae" of the column is continually updated. In particular, the number of injections conducted on the column which is stored on the identification module 3 is increased by one for every new injection. This is performed by means of an appropriate signal being transmitted to the identification module 3 from the control device 5, which itself also triggers the injection. Among other things, the number of injections is a measure for the usability of the column.

Other operational data, which according to the embodiment examples of the invention are continually updated on the identification module 3, are the product of the current flow through the column and the prevailing fluid pressure. The integrated product of flow and pressure, like the number of injections, is a measure for the age and/or the remaining life-span of the column. Pressure and flow are determined here by flow and pressure sensors employed in the chromatograph and transmitted via the control device 5 and the transmit-receive device 4 to the identification module 3. As an alternative, or in combination with the operational data mentioned above, the integrated product of pressure and time or the respective pressure values of the injections conducted can be updated on the identification module.

In a data storage device of the control device 5, certain threshold values are contained for the number of injections, the pressure, and/or the integrated product of pressure and flow. These values can be changed if necessary by the user, by means of the input-output device 10. If these threshold values for a column 3 are reached, this is determined by the control device 5 which causes an appropriate message to appear on the screen 8. The user's attention can thus be drawn at an early stage to the fact that the column will very soon be spent and has to be replaced by a new one. According to one embodiment of the invention, on the screen 8 a graphical symbol 11 appears, which for example remains green as long as the aforementioned threshold values for the column are not yet reached, and which becomes yellow once the threshold values are reached.

It is further possible to enter maximum values for pressure, temperature and the pH value on the identification module, which may not be exceeded without causing damage to the column. If during operation of the chromatograph the control device 5 recognizes with the aid of appropriate sensors that these maximum values have been exceeded, the control device 5 sees to it that either the measurement is stopped or that a warning for the user is issued on the screen.

A further embodiment of the invention relates to applications in which longer-term chromatographic measurements are conducted without supervision by the user. An example for these is the automatic chromatographic analysis of a large number of sample substances, which are injected into the column one after the other using an autosampler. Since analyses of this kind can take several hours or even days, it is possible that in the middle of such an analysis the column is spent. As no user is present to recognize this, for instance due to a symbol 11, described above, being displayed on the screen 8, the remaining analyses would be conducted under bad column conditions and could even be worthless.

This problem is solved according to an embodiment of the invention in the following manner: when the user enters the measurement program to be conducted, the control device 5 also checks whether this measurement program can in fact be conducted with the column currently in place in the chromatograph. Thus, for example, the control device calculates the number of injections to occur in the measurement program to be conducted, adds these to the number of injections stored on the identification module 3 and compares the sum with the threshold value mentioned above. If the threshold value is exceeded, this is displayed for the user on the screen. The user can then replace the column with a new column, with which the planned measurement program can be conducted without any problem.

An alternative solution to the problem described above consists in the chromatograph containing several columns and a switching valve for switching between different columns, and having the system switch to another, unused column if the threshold value mentioned for the column used is exceeded during the measurement program. This switching takes place automatically under the control of the control device 5, so that the entire program can be conducted without user supervision. A further alternative solution consists in the use of an external contact controller, for example a robot, which replaces the used column with a new column during the measurement program.

It is obvious that the threshold value mentioned does not necessarily have to relate to the number of injections, but that other parameters stored on the identification module can also be used, such as the integrated product of pressure and flow. In addition, the threshold value does not have to be related to a single parameter, but it can be defined by means of a combination of different parameters. One of these parameters, for example. could be the column temperature integrated over the operating time.

A further application of the invention consists in the arrangement of the control device 5 in such a manner that when a new column equipped with an identification module is inserted in the chromatograph it is first checked whether the column is in fact suitable for conducting the analysis intended by the user. It is well-known, that certain types of column are better suited to certain kinds of chromatographic analyses than others, and that certain types of column are unsuitable for certain analyses. The control device 5 then compares the description of the column type on the identification module with the analysis entered by the user and if necessary issues a message for the user on the screen 8, to the effect that the column currently in place is not suitable or not optimal for the analysis planned.

Figure 2:
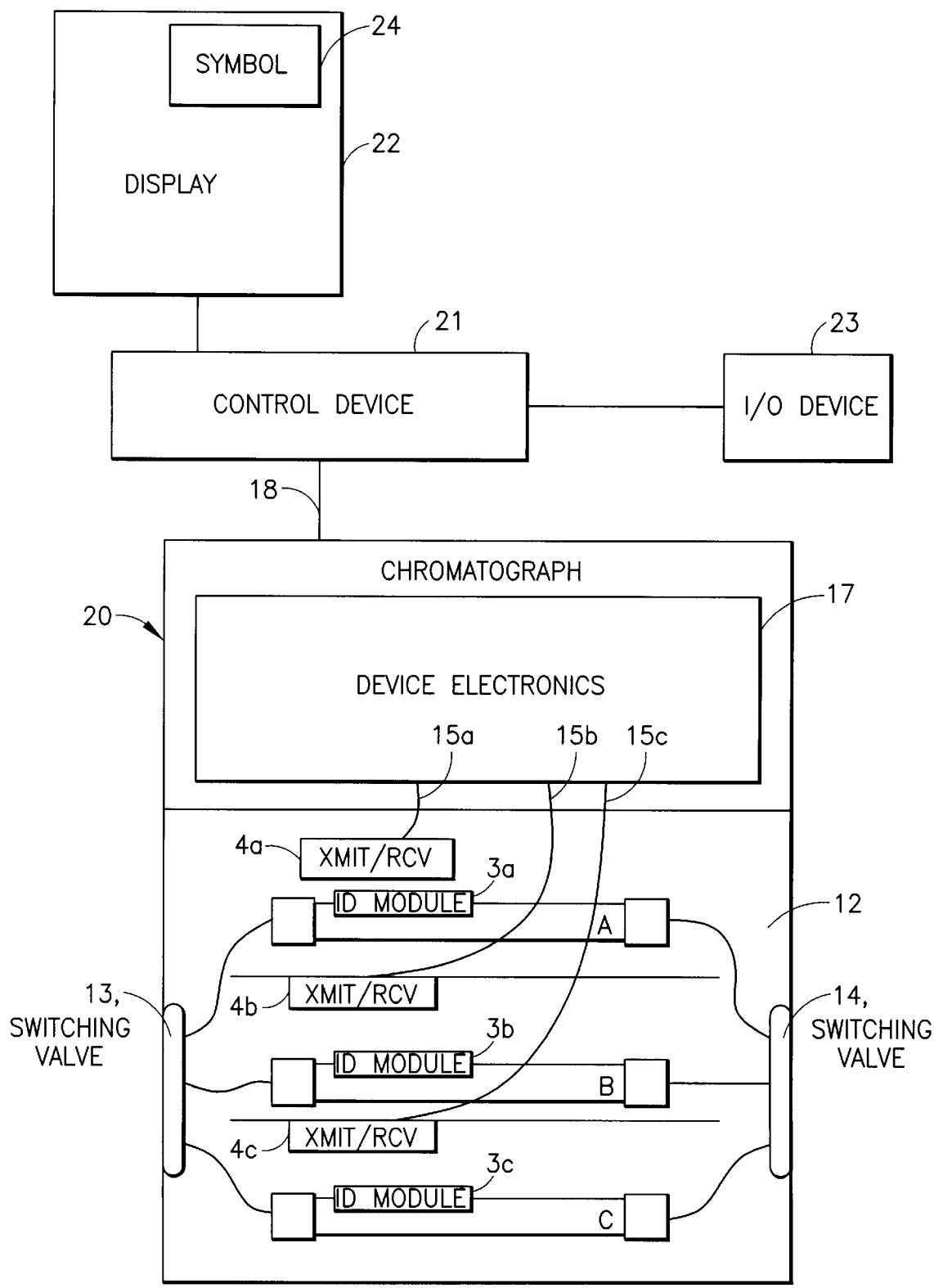
FIG. 2 shows an embodiment of the invention with several columns.

In a further development of this application it is also possible for the column best suited to an analysis to be automatically selected and the sample to be analyzed applied to it. This can be achieved by having several columns of different types available in the chromatograph 20 where these columns can be placed in the chromatographic path as desired by means of switching valves. In FIG. 2 an embodiment of this kind is depicted schematically. Three different separation columns A, B and C are shown there, which are arranged in a housing 12, for instance an oven. Attached to each column is an identification module 3a, 3b or 3c, which contains information about the respective column.

The entrance of each column is connected to a switching valve 13 via which the substances to be separated are applied. By means of the switching valve 13, one of the three columns can be selected at any time. The outputs of the separation columns are connected to another switching valve 14, from which the separated substances are transported further, for example to a detector. Transmit-receive devices 4a, 4b, 4c send and/or receive information from the corresponding identification modules 3a, 3b, 3c. The transmit-receive devices 4a, 4b, 4c are each connected via electric connections 15a, 15b, 15c to the device electronics 17 of the chromatograph. These in turn are connected via an electric connection 18 to a control device 21, to which as in the embodiment shown in FIG. 1 a display device 22 and an input/output device 23 are connected. Activation of the switching valves 13, 14 is controlled by the control device 21. On the display device 22 a graphical symbol 24 can be depicted, as explained in conjunction with FIG. 1.

An alternative method of selecting the column consists in employing the most suitable column each time by means of a robot. The advantage of both embodiments is that the degree of automation of chromatographic analyses is increased, so that a higher number of samples with different chromatographic demands on the separation columns can be analyzed without intervention or supervision by a user.

According to a further embodiment of the invention the identification module contains data about a reference analysis conducted on the corresponding column. Such a reference analysis is conducted with the new column under known conditions with a standard sample and the corresponding chromatographic data is stored on the identification module. During the life-span of the column such standard injections are conducted repeatedly and compared with the reference analysis originally conducted. From the comparison it is deduced whether the column is still supplying satisfactory results or whether it has to be exchanged. One criterium, for example, could be whether certain components represented in the chromatogram are sufficiently well separated from one another to be evaluated quantitatively.

In a further development of this embodiment, correction factors are obtained from the comparison of the original reference analysis with the current injection. With these correction factors, changes in the chromatogram which are attributable to the ageing of the column can be corrected.

It is clear that the embodiment examples described above are equally applicable for separation columns in liquid chromatography, gas chromatography, capillary electrophoresis, capillary electrochromatography or any other separation method. Other applications will be described below.

Figure 3:
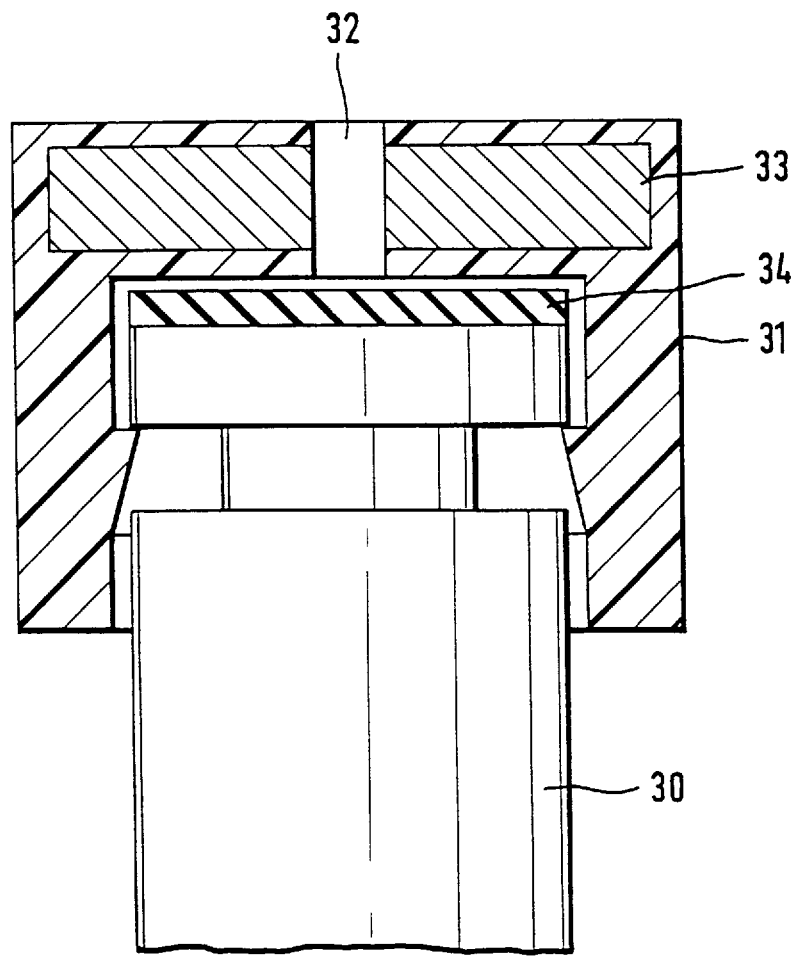
FIG. 3 shows another embodiment example of the invention in conjunction with a sample vessel for analytical measurement techniques.

In FIG. 3 a re-usable identification module 31 is shown which can be attached to a sample vessel 30 for analytical measurement techniques. Sample vessels of this kind are employed for example in liquid chromatography or capillary electrophoresis in conjunction with an autosampler. The identification module 31 is clamped to the vessel 30 in such a way that it can be removed again by the user. The preferred location for the identification module is the upper section of the vessel. Hereby it is guaranteed that the identification module is easily accessible and that the orientation of the vessel has no effect on module reading out or writing processes.

The electronic components 33 of the identification module are encapsulated in plastic material. The identification module has an opening 32 in the center in which the needle of the autosampler can be inserted in order to pierce the septum 34, so that the sample can be removed from the vessel 30 through the needle.

The electronic assemblies which communicate with the identification module 31 and which supply the energy it needs for its operation are integral components of the transport mechanism of the autosampler, for example the gripper arm. The identification module can be read by moving the gripper arm over the upper section of the sample vessel 30 without touching the vessel. In this manner the autosampler can scan the vessels in the autosampler tray and make the corresponding data available to the user or to the control device. Further, measurement series with different sample vessels can be defined, whereby the user enters the identification number stored on the identification module instead of the hitherto usual position of the vessel within the autosampler tray. After the autosampler has brought the vessel 30 up to the injection opening of the analytical measuring instrument, the identification number is again read out in order to verify the identity of the sample. The identification module 31 can also contain further information aside from an identification number, for example information about possible pre-treatment of the sample and necessary methods for analyzing the sample and about the management of the sample from its entry to the analysis certificate.

A further possible application of an identification module is presented by the sample tray of an analytical instrument. Here, the identification module is incorporated in the exchangeable carrier and contains information about the carrier itself and (indirectly) about the samples in the carrier. When a sample is treated or analyzed, this information is updated. One piece of information on the identification module could for example be the name of the user. A further possibility is for each user only to use those sample carriers which "belong to him/her": the product number of the carrier and the serial number is directly allocated to the user. At the location at which samples are taken or treated, information about the current date and time and an identification of that location is written to the identification module.

An identification module according to the invention can also be employed in conjunction with detector lamps. Detector lamps age with time, which is noticeable in terms of bad measurement results. According to the invention the lamp is equipped with an identification module on which the accumulated time the lamp has been on is recorded. As a measure for the length of time the lamp has been on, either the integrated lamp current or a signal from the detector showing that the lamp is on may be used. When on the identification module the accumulated time the lamp has been on exceeds a predetermined threshold value an appropriate message is issued to the user. On the identification module there is also information about the product number and the serial number of the lamp. In addition, according to a further development of the invention the identification module contains a reference intensity spectrum of the lamp. This reference intensity spectrum can be compared with the current intensity spectrum of the lamp at any time, in order, if required values are deviated from, to give the user an appropriate warning on a display device or to cause the lamp to be changed automatically or to use the deviations found to correct the measurements.

An identification module can also be used for a detector cell. In general the user can choose between different detector cells for different applications. An identification module integrated in a detector cell contains information about the cell type, the path length of the cell, cell volume and, for example, applications of the cell. Exchange of the cell can take place automatically with the aid of a cell exchange device.

Not only can the invention be used for single pieces of analytical equipment (as described above), but also, in an especially advantageous manner, in analytical systems which consist of several connected pieces of analytical equipment. One embodiment of this kind is described below with reference to FIG. 4.

In the example shown the analytical measurement system 40 comprises the analytical equipment 41, 42, 43 and 44, for example detection device, separation device with separation column, autosampler and pump device. The device 41 contains a sample cell 46 and a lamp 47 which are both equipped with an identification module 48 and 49 according to the invention. The transmit-receive devices 50 and 51, which exchange information with the identification modules 48 and 49, are connected to the device electronics 52. The device electronics 52 are connected via a control cable 53 to a control device 54. The device 42 contains a first separation column 55 with an identification module 56 and a second separation column 57 with an identification module 58. The accompanying transmit-receive devices 59 and 60 are connected to the device electronics 61 which in turn are connected to the control device 54. The device 43 contains a sample carrier with a number of sample vessels (sample tray) 62, to which an identification module 66 is attached, which communicates with a transmit-receive device 67. In addition, a sample vessel 63 is depicted with an identification module 64, which communicates with a transmit-receive device 65. The transmit-receive devices 65 and 67 are connected to the device electronics 68 and these in turn are connected to the control device 54. The device 44 contains a pump head 69 with an identification module 70. The identification module exchanges information with the transmit-receive device 71 which is connected to the device electronics 72. The device electronics 72 are connected via control cable 53 to the transmit-receive device 54. In addition, another sample transport apparatus (not shown)—for example a sample loop—can be provided, in which the sample to be analyzed is inserted from the sample vessel 63.

Figure 4:
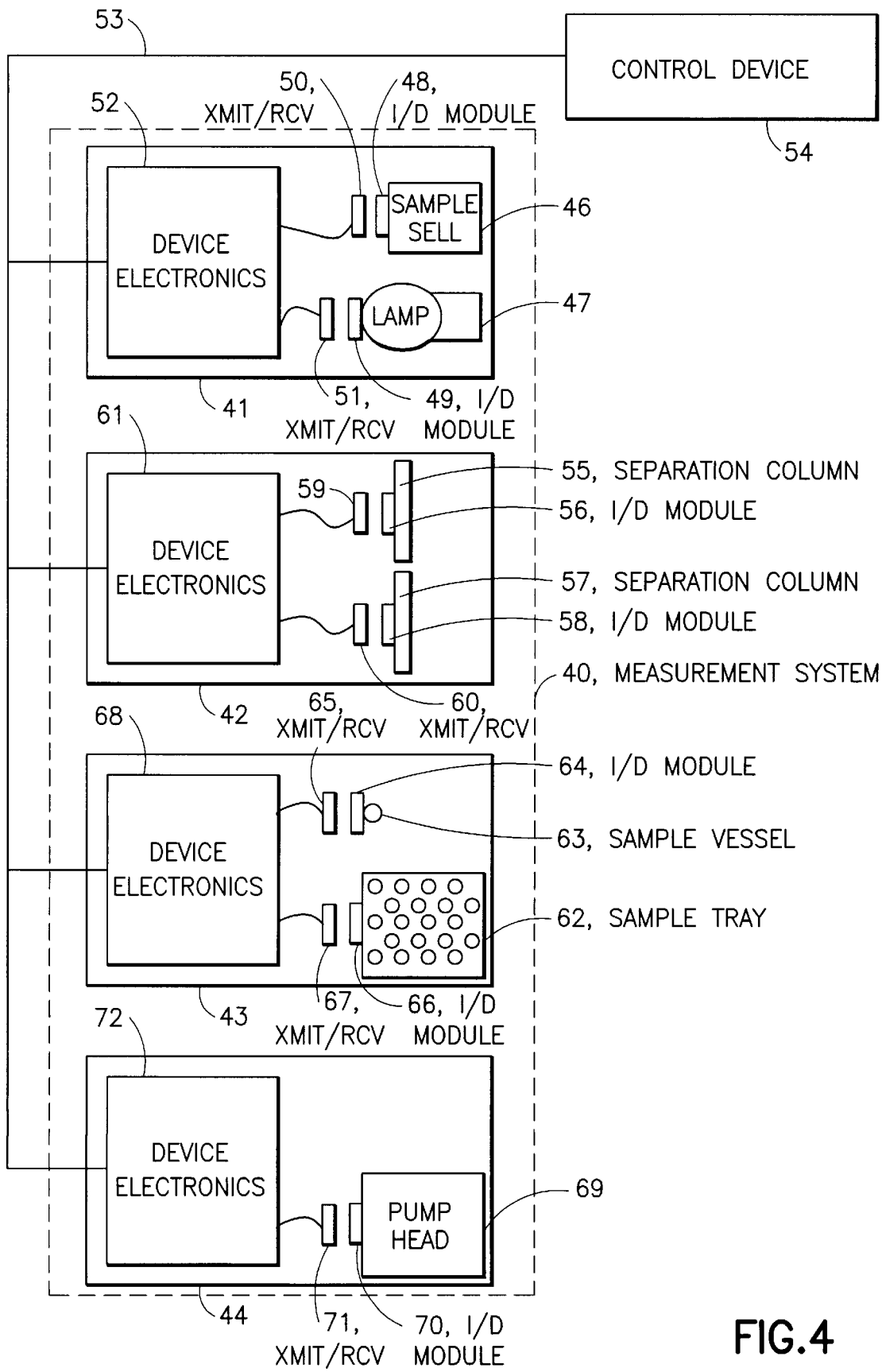
FIG. 4 shows another embodiment example of the invention in an analytical measurement system with several devices.

In the analytical system depicted in FIG. 4 the information read out of the identification modules of the different devices 41, 42, 43 and 44 is evaluated by the control device 13 and on the basis of this the operation of the entire system is controlled. In addition, the control device also causes new information to be written to the identification modules if certain parameters of the exchangeable parts, to each of which an identification module is attached, have changed, for example the number of injections conducted with the column, the length of time the lamp has been on, the pre-treatment of the sample, etc.

A system of the kind depicted in FIG. 4 is characterized among other things in that it enables the automatic processing of complex analytical sequences with a large number of samples and with different separation methods. Before a sequence is started, a check may be performed as to whether the parts equipped with an identification module are of a kind and in a condition which will allow the planned sequence to be processed in its entirety. If this is not the case, either a message is issued on a display device so that the user can exchange the part concerned, or the exchange takes place automatically, controlled by the control device 54. As an alternative to this, the sequence could also be interrupted by the control device if on the basis of the information stored on an identification module unacceptable conditions for the continuation of the measurement are determined. Altogether, the invention therefore enables integrated system monitoring and system control with increased reliability in addition to a high degree of versatility and a minimum of user supervision, or indeed entirely without user supervision.

The invention also makes it possible to set up an electronic component management system of exchangeable parts equipped with an identification module. If for example the identification module reports that the accompanying exchangeable part has to be replaced, an appropriate order for a new part is automatically sent to a suitable stock-room. Finally, the invention also makes it possible to monitor an analysis at a location at a great distance from the laboratory, if the information on the identification modules (possibly also further information) is transmitted to this location.

It is obvious that numerous variations of the embodiment examples above described which still lie within the framework of the concept of the present invention, are possible. For example there are several possibilities for data transfer between the identification module and the transmit-receive device: apart from the high-frequency transmission described, transmission by means of infrared or other radiation of the electromagnetic spectrum could also be employed. In addition, a cable connection between the identification module and the transmit-receive device could be provided. However, a cable-free connection is preferable because it is more user-friendly since the user does not have to connect or disconnect any cable when inserting or removing the exchangeable part.

We claim:

1. Apparatus for the recognition of an exchangeable part in analytical measuring instruments, with an identification module connected to the exchangeable part and a transmit-receive device which can receive information signals from the identification module and send information signals to the identification module, wherein:

a control device is connected to the transmit-receive device, which triggers the reading out of the information stored on the identification module and which causes a message to be displayed on a display device if the information read out of the identification module fulfills predetermined identification information conditions.

2. Apparatus in accordance with claim 1, wherein the transmit-receive device controlled by the control device queries the information module periodically about a stored piece of identification information and the control device causes an appropriate message to be displayed on the display device if the identification information is no longer received by the transmit-receive device or if this information has changed since the last query.

3. Apparatus in accordance with claim 1, wherein the control device causes a warning to be displayed on the display device if the information read out of the identification module characteristic for the quality of the exchangeable part reaches a predetermined threshold value.

4. Apparatus for recognizing an exchangeable part in analytical measuring instruments, with an identification module connected to the exchangeable part a transmit-receive device which can receive information signals from the identification module and send information signals to the identification module, wherein a control device is connected to the transmit-receive device, which triggers the reading out of the information stored on the identification module and which causes the automatic replacement of the exchangeable part or a switch to another exchangeable part, if the information read out of the identification module does not fulfill predetermined information conditions.

5. Apparatus in accordance with claim 4, wherein the exchangeable part is a chromatographic column and the information read out of the identification module is the number of injections conducted with the column, the permitted maximum pressure over the column or the integrated product of pressure and volume rate through the column.

6. Apparatus in accordance with claim 5, wherein a second chromatographic column is provided, as well as a column switching apparatus by means of which the system can switch from the first column equipped with the identification module to the second column, if the number of injections or the integrated product of pressure and volume rate read out of the identification module of the first column reaches a predetermined threshold value.

7. Analytical measurement system with several analytical devices which contain exchangeable parts comprising:

identification modules, each attached to one of the exchangeable parts, transmit-receive devices which can receive information signals from an identification module and send information signals to an identification module and a control device which evaluates the information from the identification modules.

8. Apparatus in accordance with claim 7, wherein the exchangeable parts belong to the following group of parts: sample cell, lamp, column, sample tray, sample vessel, pump head, and sample transport apparatus.

* * * * *